US009662382B2

(12) United States Patent
Jacobs

(10) Patent No.: US 9,662,382 B2
(45) Date of Patent: May 30, 2017

(54) VACCINE TO PROTECT A RUMINANT AGAINST PNEUMONIA CAUSED BY PASTEURELLA MULTOCIDA

(71) Applicant: Intervet Inc., Summit, NJ (US)

(72) Inventor: Antonius Arnoldus Christiaan Jacobs, Boxmeer (NL)

(73) Assignee: Intervet Inc., Madison, NJ (US)

( * ) Notice: Subject to any disclaimer, the term of this patent is extended or adjusted under 35 U.S.C. 154(b) by 0 days.

(21) Appl. No.: 14/647,337

(22) PCT Filed: Nov. 28, 2013

(86) PCT No.: PCT/EP2013/074930
§ 371 (c)(1),
(2) Date: May 26, 2015

(87) PCT Pub. No.: WO2014/083091
PCT Pub. Date: Jun. 5, 2014

(65) Prior Publication Data
US 2015/0297704 A1  Oct. 22, 2015

(30) Foreign Application Priority Data
Nov. 29, 2012  (EP) ..................... 12194759

(51) Int. Cl.
| | | |
|---|---|---|
| *A01N 63/00* | (2006.01) | |
| *A61K 39/102* | (2006.01) | |
| *A61K 39/155* | (2006.01) | |
| *A61K 39/265* | (2006.01) | |
| *C12N 7/00* | (2006.01) | |
| *A61K 39/00* | (2006.01) | |

(52) U.S. Cl.
CPC .......... *A61K 39/102* (2013.01); *A61K 39/155* (2013.01); *A61K 39/265* (2013.01); *C12N 7/00* (2013.01); *A61K 2039/522* (2013.01); *A61K 2039/5254* (2013.01); *A61K 2039/543* (2013.01); *A61K 2039/544* (2013.01); *A61K 2039/552* (2013.01); *A61K 2039/70* (2013.01); *C12N 2710/16734* (2013.01); *C12N 2760/18534* (2013.01); *C12N 2760/18634* (2013.01)

(58) Field of Classification Search
CPC .................................................. A61K 39/102
See application file for complete search history.

(56) References Cited

U.S. PATENT DOCUMENTS

| | | | |
|---|---|---|---|
| 4,132,775 A | 1/1979 | Volenec et al. | |
| 5,256,415 A | 10/1993 | Corstvet et al. | |
| 2004/0074446 A1* | 4/2004 | Hawn ................ | A01K 29/00 119/174 |
| 2005/0106185 A1* | 5/2005 | Briggs ................ | A61K 39/102 424/255.1 |
| 2005/0208060 A1* | 9/2005 | Haensler ................ | A61K 39/21 424/184.1 |
| 2008/0241192 A1 | 10/2008 | Kumar et al. | |
| 2010/0062017 A1 | 3/2010 | Luo | |
| 2011/0165090 A1 | 7/2011 | Cravens | |
| 2015/0297704 A1 | 10/2015 | Jacobs | |
| 2016/0287690 A1 | 10/2016 | Jacobs | |

FOREIGN PATENT DOCUMENTS

| | | |
|---|---|---|
| EP | 650734 A1 | 5/1995 |
| EP | 0810283 A2 | 12/1997 |
| WO | 2001049263 A1 | 7/2001 |
| WO | 2004006851 A1 | 1/2004 |
| WO | 2004017990 A1 | 3/2004 |
| WO | 2005003330 A2 | 1/2005 |
| WO | 2005077409 A1 | 8/2005 |
| WO | WO2006122586 A1 | 11/2006 |
| WO | 2008118902 A1 | 10/2008 |

OTHER PUBLICATIONS

Confer, A.W. et al., Antibody responses of cattle to outer membrane proteins of Pasteurella multocisa A:3, AJVRA, Oct. 1996, pp. 1453-1457, vol. 57, No. 10, EP.
European Search Report for 2194759.2 mailed on Apr. 8, 2013, 8 pages.
International Search Report PCT/EP2013/074930 mailed on Jan. 22, 2014.
Kirkpatrick J.G. et al., Effect of age at the time of vaccination on anitbody titers acid feedlot performance in beef calves, JAVMA, Jul. 1, 2008, pp. 136-142, vol. 233, No. 1, EP.
Panciera, R.J. et al., Bovine pneumonic pasteurellosis; effect of vaccination with live *Pasteurella* species, American Journal of veterinary research, Dec. 1984, pp. 2538-2542, vol. 45. issue 12.
Hodgson, J.C., Efficacy of vaccination of calves against hemorrhagic septicemia with a live aroA derivative of Pasteurella multocida B:2 by two different routes of administration, Infection and Immunity, Mar. 1, 2005, pp. 1475-1481, vol. 73, No. 3.
Allen et al, Changes in the Bacterial Flora of the Upper and Lower, Can J Vet Res, 1992, pp. 177-183, vol. 56.
Confer, A.W. et al., Bovine pneumonic pasteurellosis: Immunity to Pasteurella haemolytica, JAVMA, Nov. 15, 1988, pp. 1308-1316, vol. 193, No. 10.
Cravens, R L, Document ID: US 20110165090 A1, DERWENT-ACC-No. 2011-H73332, pp. 1-3, Jul. 2011.
Dabo et al, Pasteurella multocida and bovine respiratory disease, Animal Health Research Reviews, 2008, pp. 129-150, 8(2).
Frank, G.H. et al., Effect of intranasal exposure to leukotoxin-deficient Mannheimia haemolytics at the time of arrival at the feedyard on subsequent isolation of M haemolytica from nasal secretions of calves, AJVR, May 2003, pp. 580-585, vol. 64, No. 5.

(Continued)

*Primary Examiner* — Albert Navarro

(57) ABSTRACT

The present invention pertains to a vaccine comprising live attenuated *Pasteurella multocida* bacteria for protection of a ruminant against pneumonia caused by *P. multocida* by administration of the vaccine to the upper respiratory tract of the ruminant via intranasal atomization of the vaccine. The invention also pertains to a method to use the vaccine to protect a ruminant against pneumonia caused by *P. multocida* bacteria.

9 Claims, No Drawings

(56) References Cited

OTHER PUBLICATIONS

Frank, G.H. et al., Effects of vaccination prior to transit and administration of florfenicol at time of arrival in a feedlot on the health of transported calves and detection of Mannheimia haemolytica in nasal secretions, AJVR, Feb. 2002, pp. 251-256, vol. 63, No. 2.

Highlander et al, Inactivation of Pasteurella (Mannheimia) haemolytica Leukotoxin, Infection and Immunity, Jul. 2000, p. 3916-3922, vol. 68, No. 7.

Jericho, K.W.F. and Langford, E.V., Aerosol vaccination of calves with Pasteurella haemolytica against experimental respiratory disease, Can. J. comp. Med., Jul. 1982, pp. 287-292, vol. 46.

Jericho, K.W.F., Histological changes in lungs of calves exposed to an aerosol of Pasteurella haemolytica, J. Comp. Path., 1989, pp. 87-99, vol. 101.

Kisiela et al, Identification of Mannheimia haemolytica Adhesins Involved in, Infection and Immunity, Jan. 2009, p. 446-455, vol. 77, No. 1.

Xue, W. et al., Immunogenicity of a modified-live virus vaccine against bovine viral diarrhea virus types 1 and 2, infectious bovine rhinotracheitis virus, bovine parainfluenza-3 virus, and bovine respiratory syncytial virus when administered intranasally in young calves, Vaccine, 2010, pp. 3784-3792, 28.

* cited by examiner

VACCINE TO PROTECT A RUMINANT AGAINST PNEUMONIA CAUSED BY PASTEURELLA MULTOCIDA

CROSS-REFERENCE TO RELATED APPLICATIONS

This application is a national stage entry under 35 U.S.C. §371 of PCT/EP2013/074930, filed on Nov. 28, 2013, which claims priority to EP Application No. EP12194759.2, filed on Nov. 29, 2012. The content of PCT/EP2013/12194759.2 is hereby incorporated by reference in its entirety.

The present invention pertains to a vaccine to protect a ruminant against pneumonia caused by *Pasteurella multocida*. The invention also pertains to the manufacture of such a vaccine and a method for protecting a ruminant against pneumonia caused by *Pasteurella multocida*.

*Pasteurella multocida* bacteria in general may cause disease in wild and domesticated animals as well as humans. The bacterium can be found in fowl, felines, canines, rabbits, cattle and pigs. In birds, *Pasteurella multocida* may cause avian cholera. The *Pasteurella multocida* serotype A:1 is most associated with avian cholera. *Pasteurella multocida* serotype D may cause atrophic rhinitis in pigs. Certain serotypes, such as B:2 may cause haemorrhagic septicaemia, a systemic infection in ruminants, for example in bovine (i.e. animals that belong to the genus *Bos*, such as cows, steers, oxen, any other cattle, buffaloes etc). The bacteria that belong to serogroup A, in particular serotype A:3, may cause pneumonia in ruminants, in particular in bovine. Pneumonia is a local infection of the lower respiratory tract (in bovine often associated with bovine respiratory disease). The present invention pertains to those bacteria that cause such pneumonia in ruminants, in particular bovine.

The *Pasteurella multocida* bacteria that cause pneumonia in ruminants are a commensal of the upper respiratory tract of these animals (Allen et al.; Can. J. Vet. Res., 1992, 56: 177-183). In other words, the upper respiratory tract (including the nasal cavity, pharynx and larynx) of most animals harbors these bacteria without causing any physiological reaction such as disease or an immune response against these bacteria. Induction of disease is often associated with stress, especially from transportation, or infection with pathogenic viruses. Protection against the disease (which includes aiding in preventing, or ameliorating the disease) may take place by systemic vaccination of animals with a vaccine comprising live or killed *P. multocida* bacteria as commonly known in the art (see e.g. S. M. Dabo et al. in *Animal Health Research Reviews*, 8 (2), 2008, 129-150). In general, a vaccine comprising live bacteria may be preferred when vaccinating very young animals (i.e. less then 3-4 weeks of age). A killed vaccine namely is generally less effective in the presence of maternally derived antibodies. However, a live vaccine on its turn may be less safe in such young animals. In particular, shock may occur after vaccinating young animals with live attenuated *Pasteurella multocida* bacteria of the pneumonia causing serotypes.

Confer et al. (Amer. J. of Vet. Res., 1996, 57: 1453-1457) studied antibody responses against *Pasteurella* outer membrane proteins, following vaccination and challenge of calves of 5-8 months old. The vaccines were prepared from a field isolate of *P. multocida* A:3, and were administered twice with a 7 day interval. They consisted of either live bacteria administered subcutaneously or by whole body exposure to an aerosol, or of killed bacteria administered by aerosol exposure.

The object of the invention is to provide a vaccine that protects, i.e. at least aids in preventing, ameliorates, actually prevents or cures, against pneumonia caused by *Pasteurella multocida*, which vaccine is safe in young animals.

To this end, a vaccine for administration to the upper respiratory tract of a ruminant has been devised, which vaccine comprises live attenuated *Pasteurella multocida* bacteria, the administration taking place via atomisation of the vaccine. That is, the vaccine is administered by spraying it as a mist of fine particles (heaving a volume averaged mean diameter of less than 200 μm) to reach at the upper respiratory tract of the animal. The administration of the attenuated *Pasteurella multocida* bacteria to the upper respiratory tract is expected to be inherently safe since even wild-type bacteria generally do not induce disease when present in the upper respiratory tract. However, it was not expected beforehand that an immune response (let alone an adequate response) would be raised against the live attenuated *Pasteurella multocida* bacteria: even wild-type bacteria when present in this part of the respiratory tract do not induce an immune response under normal circumstances. Surprisingly, by administering live attenuated *Pasteurella multocida* bacteria (of the type that cause pneumonia in ruminants in non-attenuated form, in particular of serogroup A, in particular of serotype A:3) to the upper respiratory tract in the form of a fine mist of particles, an adequate immune response against the live attenuated *Pasteurella multocida* bacteria is induced. It is noted that atomisation can be performed not only when the vaccine is in a liquid form (the particles then being droplets), but also when the vaccine is in a solid form (e.g. a lyophilized powder or cake of the strains in a stabiliser), in which case the vaccine may be spread as a fine powder, typically a powdered freeze-dried cake of the bacterium in a stabiliser matrix. It is estimated that a lower limit of the atomized particles (at least the volume averaged mean diameter) of 1 μm is practical, since to obtain smaller particles a high energy input may be needed which might be impractical.

The resulting vaccine is safe in young calves (less than 3-4 weeks of age), and evokes an adequate immune response against pneumonia causing *Pasteurella multocida* bacteria (i.e. evokes an immune response that at least aids in preventing, ameliorates, actually prevents or cures pneumonia caused by *Pasteurella multocida* bacteria). Many attenuated strains of *Pasteurella multocida* are known (e.g. the streptomycin dependent strain as known from the Dabo reference mentioned here above, or strains having mutations in the genes phyB, phyA, hyaE, hyaD, hyaC, hyaB, hexD, hexC, hexB, and/or hexA as described in US 2008/0241192 (Kumar et al.). The type of attenuation is not important for the invention as such however. The invention pertains to the surprising finding that an immune response against live attenuated *Pasteurella multocida* bacteria can be elicited even if these bacteria are administered to the upper respiratory tract (where wild-type *P. multocida* is present as a commensal and does not induce an immune response), if the administration takes place via atomisation. Indeed, the type of attenuation may affect the remaining virulence of the bacterium and therefore the safety and efficacy of the vaccine. However, balancing safety and efficacy to find the desired attenuation does not relate to the above mentioned finding of the present invention.

The invention also pertains to the use of live attenuated *Pasteurella multocida* bacteria for the manufacture of a vaccine which upon administration to the upper respiratory tract of a ruminant by atomisation of the vaccine, provides protection against pneumonia caused by *Pasteurella multo-* cida bacteria, and to a method to protect a ruminant against pneumonia caused by *Pasteurella multocida* bacteria, the method comprising administration of a vaccine comprising live attenuated *Pasteurella multocida* bacteria, to the upper respiratory tract of the ruminant by atomisation of the vaccine.

Although administration to the upper respiratory tract could take place via for example the mouth of the animal (oral administration of a fine mist of particles to reach the pharynx and optionally the larynx), the vaccine preferably is for intranasal administration. Intranasal administration has proven to lead to a good mucosal immune response against the bacterium.

As is well known in the art, intranasal administration is defined as administration 'within the nose' (The American Heritage® Medical Dictionary, Houghton Mifflin Co.).

In an embodiment the atomisation provides a mist of vaccine particles having an (volume) average particle size below 50 µm in diameter. It is recognised that by having smaller particles, the larger the surface of the mucosa that can be directly reached by the vaccine. This is believed to lead to an improved immune response. A particle size below 50 µm has proven to be practical and adequate for eliciting an immune response. In a further embodiment the average particle size is between 20 and 40 µm in diameter.

In yet another embodiment the vaccine additionally comprises live attenuated parainfluenza-3 virus and live attenuated bovine respiratory syncytial virus for protection against respiratory disease caused by parainfluenza virus and bovine respiratory syncytial virus. It is believed that by adding immunogenic viruses to the vaccine, which viruses stimulate the mucosal immune response in the upper respiratory tract, an improved immune response against the *Pasteurella bacterium* will also be obtained. Although the viruses in the vaccine are immunogenic, they are attenuated and thus do not induce disease. This means that they do not cause actual pathological effects in the mucosa of the respiratory tract in contrast with their wild-type counterparts. The particular strain or type of attenuation of the virus strains is believed to be not essential for this embodiment: given the fact that the viruses are (inherently) totally unrelated to the bacterium, the specific immune response against the viruses simply cannot be essential for obtaining improved protection against the bacterium. Many attenuated live parainfluenza-3 viruses and live bovine respiratory syncytial viruses that evoke an immune response after administration to the upper respiratory tract are known in the art, such as for example from the commercially obtainable vaccines Inforce™ 3 (Pfizer Animal health), Nasalgen™ IP (Merck Animal Health), TSV-2™ (Pfizer Animal Health) and ONSET™ 5 (Merck Animal Health).

In another embodiment the vaccine comprises live attenuated infectious bovine rhinotracheitis virus. This virus is also known to be involved in respiratory diseases, in particular of bovines, and thus, protection against this pathogen is believed to further enhance the protective effect of the current vaccine against respiratory disease.

In a further embodiment, the vaccine according to the invention is for administration to bovines, preferably at an age of less than 3-4 weeks.

It is noted that a vaccine in the sense of this invention is a constitution suitable for application to an animal, comprising one or more antigens in an immunologically effective amount (i.e. capable of stimulating the immune system of the target animal sufficiently to at least reduce the negative effects of a challenge of the wild-type microorganisms), typically combined with a pharmaceutically acceptable carrier such as a liquid containing water, optionally comprising immunostimulating agents (adjuvants), which upon administration to the animal induces an immune response for treating a disease or disorder, i.e. aiding in preventing, ameliorating or curing the disease or disorder.

In general, a vaccine can be manufactured by using art-known methods that basically comprise admixing the antigens (or a composition containing the antigens) with a pharmaceutically acceptable carrier, e.g. a liquid carrier such as (optionally buffered) water or a solid carrier such as commonly used to obtain freeze-dried vaccines. For a live vaccine an immunologically effective amount is typically between $10^4$-$10^9$ CFU/dose for bacteria and between $10^3$-$10^{10}$ TCID$_{50}$/dose for viruses, although depending on the attenuation the number may be lower (for less attenuated micro-organisms) or higher (for more attenuated micro-organisms). Optionally other substances such as adjuvants, stabilisers, viscosity modifiers or other components are added depending on the intended use or desired properties of the vaccine. For vaccination many forms are suitable, in particular liquid formulations (with dissolved, emulsified or suspended antigens; typical administration volumes are between 0.1 and 10 ml, preferably between 0.2 and 5 ml, preferably 2 ml or less) but also solid formulations such as powders for atomisation devices may be suitable.

In a further embodiment, the vaccine according to the invention is applied by a single administration, preferably the administered volume is divided over both nostrils.

The term attenuated as used herein refers to the incapability of a microorganism, in particular a bacterium or virus, of inducing a full suite of symptoms of the disease that is normally associated with its virulent (often wild-type) pathogenic counterpart. It may be attenuated such that it does not replicate within a host cell or animal, or replicate at a rate which is not significantly detrimental to the cell or animal, and/or does not induce a detrimental host response. An attenuated strain may exhibit a reduced ability to survive in a host, and may contain one or more mutations in one or more virulence genes as is commonly known in the art.

In an embodiment, the vaccine according to the invention comprising live attenuated *Pasteurella multocida* bacteria for protection of a ruminant against pneumonia caused by *P. multocida* by administration of the vaccine to the upper respiratory tract of the ruminant via atomisation of the vaccine, is characterised in that the administration takes place via intranasal atomisation; the vaccine particles have an average particle size between 20 and 40 µm in diameter; the vaccine additionally comprises live attenuated parainfluenza-3 virus and live attenuated bovine respiratory syncytial virus, and optionally also comprises infectious bovine rhinotracheitis virus; the live attenuated *P. multocida* bacteria are from a streptomycin dependent strain.

The invention will further be explained based in the following examples.

EXAMPLE 1

Several atomization devices were assessed with respect to the obtained particle size. In this example, three cannulas were tested, which cannulas can be secured to standard syringes. The first cannula is the LMA MAD Nasal™ ("MAD"), available from LMA North America Inc, San Diego, Calif., USA. The second cannula is the Rispoval applicator ("Pfizer"), available from Pfizer Animal Health, Brussels, Belgium. The third cannula is a the 1" blue flex applicator nozzle available from Genesis Industries, Inc. Elmwood, Wis., USA ("Genesis").

These cannulas were tested with regular WFI (water-for-injection) and the obtained volume averaged droplet size was established using a Sympatec™ particle size analyser. The results are indicated below in Table 1.

TABLE 1

Mean droplet size with various cannulas

| Cannula type | Volume average size (diameter in μm) | Standard deviation (μm) |
|---|---|---|
| MAD | 32.8 | 8.8 |
| Pfizer | 39.5 | 4.6 |
| Genesis | 197 | Not determined |

It appears that with all three cannulas atomization of the WFI can be achieved. For the further experiments the MAD cannula was used.

EXAMPLE 2

Two groups (called Group 1 and Group 2), consisting each of twenty 2-week-old calves (clean catch and colostrum deprived) were used for the experiments. Of each group, ten calves were vaccinated once intranasally with a live *Pasteurella multocida* vaccine (see below) and ten calves were left as unvaccinated control. At five weeks of age all calves were challenged intratracheally with wild-type *P. multocida*. During 7 days after challenge, the calves were observed for the development of clinical signs of respiratory disease, in particular pneumonia. At 7 days post-challenge (or earlier in case of severe clinical signs), the calves were killed and necropsied i.e. examined for lung lesions. The experiments with the second group took place several months after the experiments with the first group.

Vaccine

In both groups, a vaccine was used containing a *Pasteurella multocida* ΔhyaE strain, derived from the wild type P1062 serotype A:3 strain which lacks the capsule (see Genbank EMBL AAK02858.1 for the gene). Just before administration, the bacteria were dissolved in WFI (water for injection) to reach about $5 \times 10^7$ CFU/ml. The actual CFU/ml was $4 \times 10^7$ for Group 1 and $8 \times 10^7$ for Group 2.

Another experiment is foreseen wherein the vaccine in addition to the above mentioned *Pasteurella multocida* strain, contains live attenuated BRSV (for example the same strains as in the product "Jencine™ 4", available from Merck Animal Health, Summit, N.J., USA) and live attenuated Pi3 virus (for example the same strain as in the product Bovilis™ IBR-PI3 live, available from MSD Animal Health, Boxmeer, The Netherlands).

Challenge Culture

For the challenge with wild type *Pasteurella* two challenge cultures were made, one homologous with the vaccine strain, the other heterologous. For the homologous challenge culture *Pasteurella multocida* P1062 was inoculated on blood agar and incubated 16-24 hours at 37° C. Subsequently, one inoculation loop was inoculated in 100 ml TPB and incubated for 7-10 hours at 37° C. For the heterologous challenge culture *Pasteurella multocida* 971/90 was inoculated on blood agar and incubated 16 hours at 37° C. Subsequently, one inoculation loop was inoculated in 100 ml TPB and incubated for 4-5 hours at 37° C.

Both cultures were diluted with PBS aiming at about $3.3 \times 10^8$ CFU/ml. It is noted that since *Pasteurella multocida* is a secondary pathogen (i.e. in general it does not cause disease), a very high challenge dose, in combination with administration to the lower part of the respiratory tract (see below), was required to induce pneumonia.

Vaccination

For each group, the calves were divided into two sub-groups (groups A and B) of 10 animals. Group A was vaccinated once intranasally by administering 2 ml of the reconstituted live vaccine in one nostril, Group B was left as unvaccinated controls. In Group 1, the vaccine was administered using a normal plastic syringe, which led to the vaccine being administered as a fluid stream, breaking up in large droplets. In Group 2 the vaccine was administered using the MAD device, which lead to atomization of the vaccine.

Challenge

At 5 weeks of age (3 weeks after vaccination) all calves were challenged intratracheally with 30 ml challenge culture, thus aiming at a challenge dose of approximately $1 \times 10^{10}$ CFU per animal. Group 1 was challenged with the homologous culture, Group 2 was challenged with the heterologous culture.

Safety Examination

In order to assess safety of the vaccine, the animals were daily observed for general health and behaviour.

Post-Mortem Examination

Seven days after challenge the animals were subjected to a post-mortem examination with special attention to the lungs. For each lung lobe the % consolidation was recorded, which corresponds to actual pneumonia. Also, *Pasteurella multocida* was reisolated from post-mortem samples in order to determine the bacterial load of the lungs with the bacterium. For this, tissue samples were excised from eight standard sites representative of the lobes of each half of the lung (4 sites per half); diseased tissue was preferentially selected for each site, if it was present. The mirror image samples (the two samples of the equivalent lobe on each half) were pooled to give 4 samples per calf. Each pooled sample was submerged in boiling water for 3 seconds, homogenized, serially 10-fold diluted and inoculated (100 μl) on blood agar plates and then incubated for 16-24 hours at 37° C.

Statistical Analysis

Lung consolidation and re-isolation scores were evaluated by the Mann-Whitney U test using the statistical programme Statistix™ for Windows.

Results

Safety

Vaccination with both vaccines appeared to be safe, and no clinical signs related to pneumonia or shock were observed.

Pneumonia and Re-Isolation

In Tables 2 and 3, the results for the post-mortem scores for pneumonia (percentage lung consolidation) and re-isolation of *Pasteurella multocida* ($\log_{10}$ CFU) are shown for Group 1. As can be seen, the results indicate that no substantial protective effects could be obtained with the live *Pasteurella multocida* vaccine by administration of the vaccine in the form of a liquid stream breaking up into large droplets. The actual uncertainty of any effect was 0.43 for the lung consolidation and 0.60 for the re-isolation scores.

In Tables 4 and 5, corresponding results are indicated for Group 2, vaccinated with the live vaccine administered to the upper respiratory tract by atomization of the vaccine and challenged with a heterologous PM (*P. multocida*) strain (which when compared to a homologous challenge typically makes it more difficult to obtain protection). As can be seen, the lung lesion scores were substantially reduced by about 50%. Although the statistical analysis revealed that there is still an uncertainty of 0.12 (which is actually quite low given the small group of animals), it is clear that there is at least partial protection, despite the fact that the challenge was with a heterologous wild-type *P. multocida*. With respect to re-isolation, there appears to be a decrease in bacterial load by $1.5^{10}$ logs, which equals a decrease in bacterial load of about a factor 30 (that is a factor ten times as large as in Group 1). The statistical uncertainty is only 0.10 despite the fact that the experiment was carried out in such a small group.

TABLE 2

% consolidation of lungs, Group 1

| Group | Vaccine | total average score |
|---|---|---|
| 1A | live PM, liquid | 82.4 |
| 1B | — | 105.6 |

TABLE 3

Re-isolation (bacterial load in the lungs), Group 1

| Group | Vaccine | total average score |
|---|---|---|
| 1A | live PM, liquid | 4.7 |
| 1B | — | 5.2 |

TABLE 4

% consolidation of lungs, Group 2

| Group | Vaccine | total average score |
|---|---|---|
| 2A | live PM, atomisation | 93 |
| 2B | — | 180 |

TABLE 5

Re-isolation (bacterial load in the lungs), Group 2

| Group | Vaccine | total average score |
|---|---|---|
| 2A | live PM, atomisation | 2.8 |
| 2B | — | 4.3 |

The invention claimed is:

1. A method to protect a ruminant against pneumonia caused by *Pasteurella multocida* bacteria, comprising administering by intranasal atomization a vaccine comprising live attenuated *P. multocida* bacteria to the upper respiratory tract of the ruminant.

2. The method of claim 1 wherein the intranasal atomization provides a mist of vaccine particles having an average size below 50 μm in diameter.

3. The method of claim 2 wherein the average particle size is between 20 and 40 μm in diameter.

4. The method of claim 3 wherein the vaccine additionally comprises live attenuated parainfluenza-3 virus and live attenuated bovine respiratory syncytial virus for protection against respiratory disease caused by parainfluenza virus and bovine respiratory syncytial virus.

5. The method of claim 4 wherein the vaccine further comprises live attenuated infectious bovine rhinotracheitis virus for protection against respiratory disease caused by infectious bovine rhinotracheitis virus.

6. The method of claim 2 wherein the vaccine additionally comprises live attenuated parainfluenza-3 virus and live attenuated bovine respiratory syncytial virus for protection against respiratory disease caused by parainfluenza virus and bovine respiratory syncytial virus.

7. The method of claim 6 wherein the vaccine further comprises live attenuated infectious bovine rhinotracheitis virus for protection against respiratory disease caused by infectious bovine rhinotracheitis virus.

8. The method of claim 1 wherein the vaccine additionally comprises live attenuated parainfluenza-3 virus and live attenuated bovine respiratory syncytial virus for protection against respiratory disease caused by parainfluenza virus and bovine respiratory syncytial virus.

9. The method of claim 8 wherein the vaccine further comprises live attenuated infectious bovine rhinotracheitis virus for protection against respiratory disease caused by infectious bovine rhinotracheitis virus.

* * * * *